(12) United States Patent
Roberts et al.

(10) Patent No.: US 10,299,876 B2
(45) Date of Patent: May 28, 2019

(54) UROLOGICAL KIT PACKAGING

(71) Applicant: C.R. BARD, INC., Murray Hill, NJ (US)

(72) Inventors: Thomas John Roberts, Bishop, GA (US); Salvatore Privitera, Mason, OH (US); Joseph Anthony Urban, Jr., Atlanta, GA (US); Jason Glithero, McDonough, GA (US)

(73) Assignee: C.R. BARD, INC., Murray Hill, NJ (US)

( * ) Notice: Subject to any disclaimer, the term of this patent is extended or adjusted under 35 U.S.C. 154(b) by 136 days.

(21) Appl. No.: 15/125,672

(22) PCT Filed: Apr. 8, 2015

(86) PCT No.: PCT/US2015/024993
§ 371 (c)(1),
(2) Date: Sep. 13, 2016

(87) PCT Pub. No.: WO2015/157462
PCT Pub. Date: Oct. 15, 2015

(65) Prior Publication Data
US 2017/0209228 A1 Jul. 27, 2017

Related U.S. Application Data

(60) Provisional application No. 62/111,084, filed on Feb. 2, 2015, provisional application No. 61/978,025, filed on Apr. 10, 2014.

(51) Int. Cl.
*A61B 50/30* (2016.01)
*A61B 17/221* (2006.01)
(Continued)

(52) U.S. Cl.
CPC ............ *A61B 50/30* (2016.02); *A61B 17/221* (2013.01); *A61M 25/002* (2013.01); *A61M 25/0017* (2013.01); *A61B 2017/22038* (2013.01)

(58) Field of Classification Search
CPC ............ A61M 25/0017; A61M 25/002; A61B 17/221
See application file for complete search history.

(56) References Cited

U.S. PATENT DOCUMENTS 4,332,322 A * 6/1982 Jaeschke ............. A61M 25/002
206/363
5,372,254 A 12/1994 Gross
(Continued)

FOREIGN PATENT DOCUMENTS

DE 202005009946 U1 9/2005
EP 0820781 A1 1/1998
(Continued)

OTHER PUBLICATIONS

U.S. Appl. No. 62/111,084, filed Feb. 2, 2015.
(Continued)

*Primary Examiner* — Richard G Louis
(74) *Attorney, Agent, or Firm* — Dorsey & Whitney LLP

(57) ABSTRACT

Packaging and kit for urological procedures. For example, the packaging 100 may secure one or more urological devices 212, 240 that may be used during a urological procedure. Furthermore, the packaging and the devices included therein may, collectively, form a urological kit.

26 Claims, 9 Drawing Sheets

(51) Int. Cl.
*A61M 25/00* (2006.01)
*A61B 17/22* (2006.01)

(56) References Cited

U.S. PATENT DOCUMENTS

| | | | | |
|---|---|---|---|---|
| 5,817,104 A * | 10/1998 | Bilitz | ................... | A61B 17/221 |
| | | | | 606/127 |
| 2004/0187438 A1 * | 9/2004 | Clarke | .................. | A61F 2/0095 |
| | | | | 53/400 |
| 2012/0261290 A1 * | 10/2012 | Limjaroen | .......... | A61M 25/002 |
| | | | | 206/364 |

FOREIGN PATENT DOCUMENTS

| | | |
|---|---|---|
| EP | 1616593 A1 | 1/2006 |
| JP | 2008104757 A | 5/2008 |

OTHER PUBLICATIONS

U.S. Appl. No. 61/978,025, filed Apr. 10, 2014.
International Search Report and Written Opinion from International Application No. PCT/US2015/024993 dated Jul. 24, 2015.

* cited by examiner

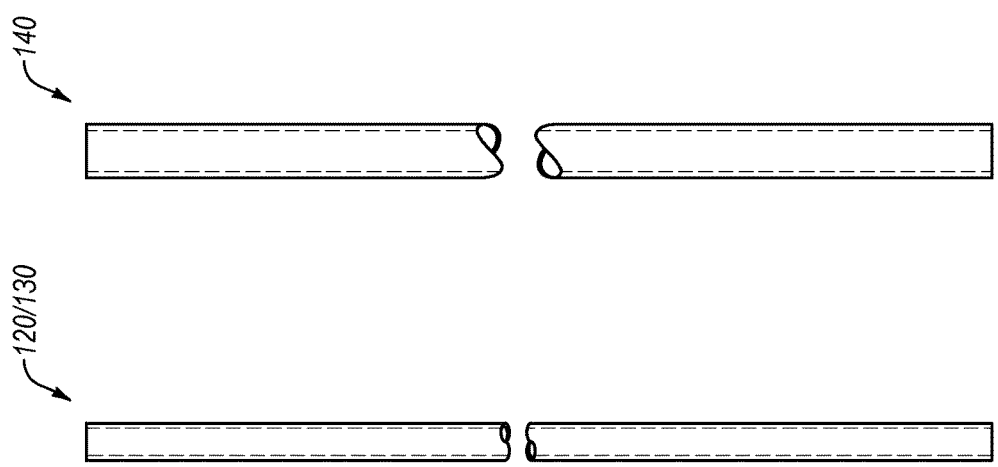
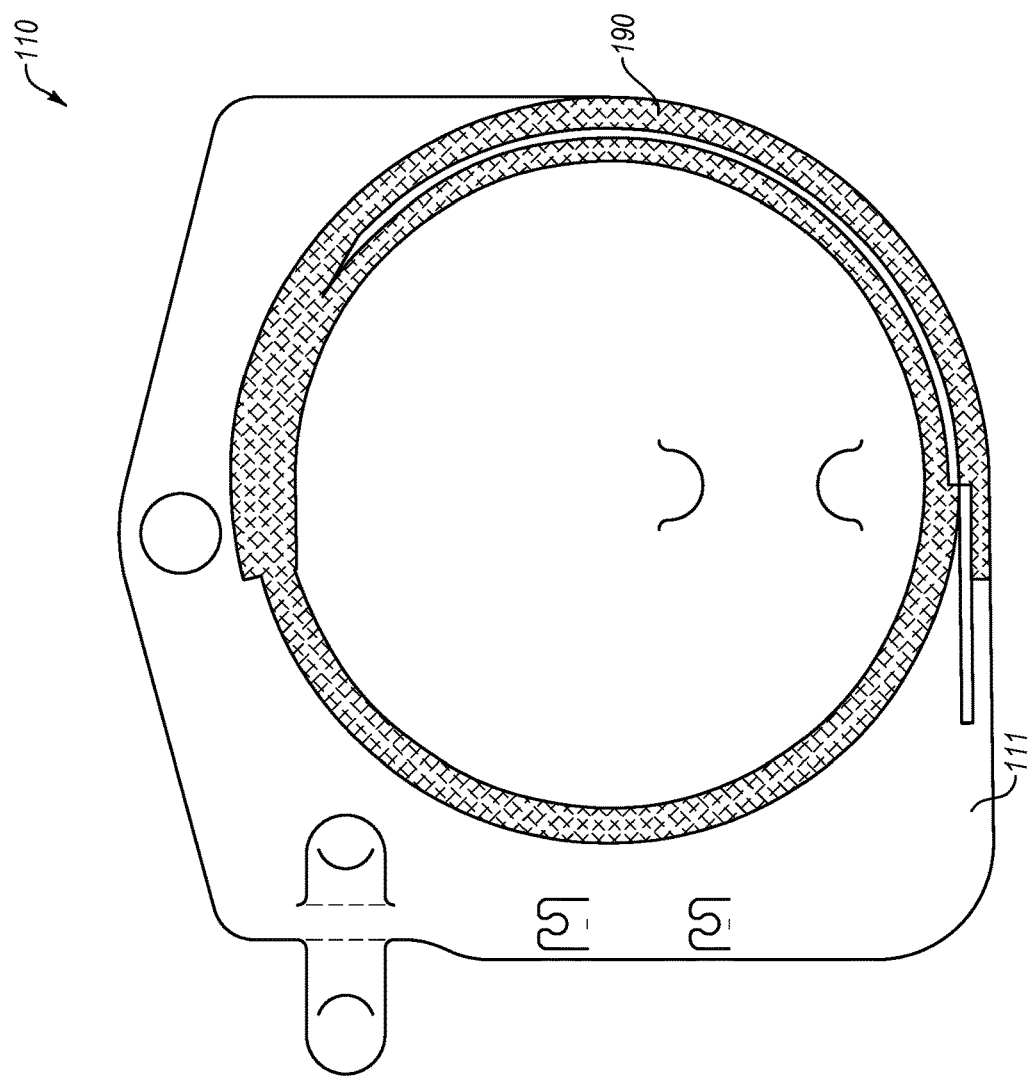

UROLOGICAL KIT PACKAGING

This application claims priority to U.S. Provisional Application 61/978,025 filed on 10 Apr. 2014 and U.S. Provisional Application No. 62/111,084 filed on 2 Feb. 2015, the disclosure of each of the foregoing applications is incorporated herein, in its entirety, by this reference.

BACKGROUND

Urological procedures may involve the use of various devices, which may vary from one procedure to the next and may depend on patient's particular circumstances. For instance, a urological procedure may involve accessing a patient's ureter with one or more devices. In some instances, storage, selection, and packaging of devices used in the urological procedure may affect duration of the procedure and/or cost of the procedure.

Accordingly, users and manufacturers of urological devices and systems continue to seek improvements that, for example, may reduce duration and/or cost of urological procedures.

SUMMARY

Embodiments described herein are directed to packaging and a kit for urological procedures as well as methods of use thereof. For example, the packaging may secure one or more urological devices that may be used during a urological procedure. Furthermore, the packaging and the one or more urological devices secured therein may collectively form a urological kit. A particular configuration of the urological kit may vary from one embodiment to the next and, among other things, may depend on the urological procedure, patient condition, user preferences, etc.

At least one embodiment includes a packaging for a urological kit. The packaging includes a base that has generally opposing first and second major faces defining a thickness of the base by a distance therebetween. The base has a width and a height that are substantially greater than the thickness thereof. The packaging for a urological kit also includes one or more tubular secured to the first major face of the base. At least one of the one or more tubular members has a looped or coiled configuration. Each of the one or more tubular members defines an internal space sized and configured to secure one or more first urological devices. Moreover, the packaging includes one or more tabs secured to or integrated with the base. The one or more tabs are sized and configured to wrap about at least a portion of at least one of the one or more first urological devices or one or more second urological devices.

Embodiments also include a urological kit. The urological kit includes a urological kit packaging that includes a base having generally opposing first and second major faces defining a thickness of the base by a distance therebetween. The urological kit packaging also includes one or more tubular members secured to the first major face of the base. At least one of the one or more tubular members has a looped or coiled configuration, each of the one or more tubular members defining an internal space. Furthermore, the urological kit packaging includes one or more tabs secured to or integrated with the base. The urological kit also includes a plurality of urological devices at least some of which include an elongated portion secured within a corresponding internal space of the one or more internal spaces of the one or more tubular members.

One or more embodiments include a system for urological procedures. The system includes a foldable base that including a first side and a second side foldably connected together or integrated with each other. The system also includes one or more tubular members secured to one or more of the first side and the second side of the foldable base. At least one of the one or more tubular members has a looped or coiled configuration, and each of the one or more tubular members defines an internal space. The system further includes two or more tabs secured to or integrated with one or more of the first side or the second side of the foldable base. The one or more tabs are sized and configured to secure at least a portion of a urological device. Moreover, at least two of the two or more tabs wrap about at least a portion of at least one of the plurality of urological devices, thereby at least partially securing the portion of the at least one urological device in the urological kit packaging.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

For better understanding, the like elements have been designated by like reference numbers throughout the various accompanying figures. Understanding that these drawings depict only typical embodiments of the invention and are not therefore to be considered to be limiting of its scope, the embodiments of the invention will be described and explained with additional specificity and detail through the use of the accompanying drawings in which:

FIG. 1C is a top view of a base of a urological kit packaging in accordance with an embodiment;

FIG. 2A is a side of view of a tubular member of a urological kit packaging for securing a urological device in accordance with an embodiment;

FIG. 2B is a side of view of a tubular member of a urological kit packaging for securing a urological device in accordance with another embodiment;

DETAILED DESCRIPTION

Embodiments described herein are directed to packaging and a kit for urological procedures as well as methods of use thereof. For example, the packaging may secure one or more urological devices that may be used during a urological procedure. Furthermore, the packaging and the one or more urological devices secured therein may collectively form a urological kit. A particular configuration of the urological kit may vary from one embodiment to the next and, among other things, may depend on the urological procedure, patient condition, user preferences, etc.

Figure 1A:
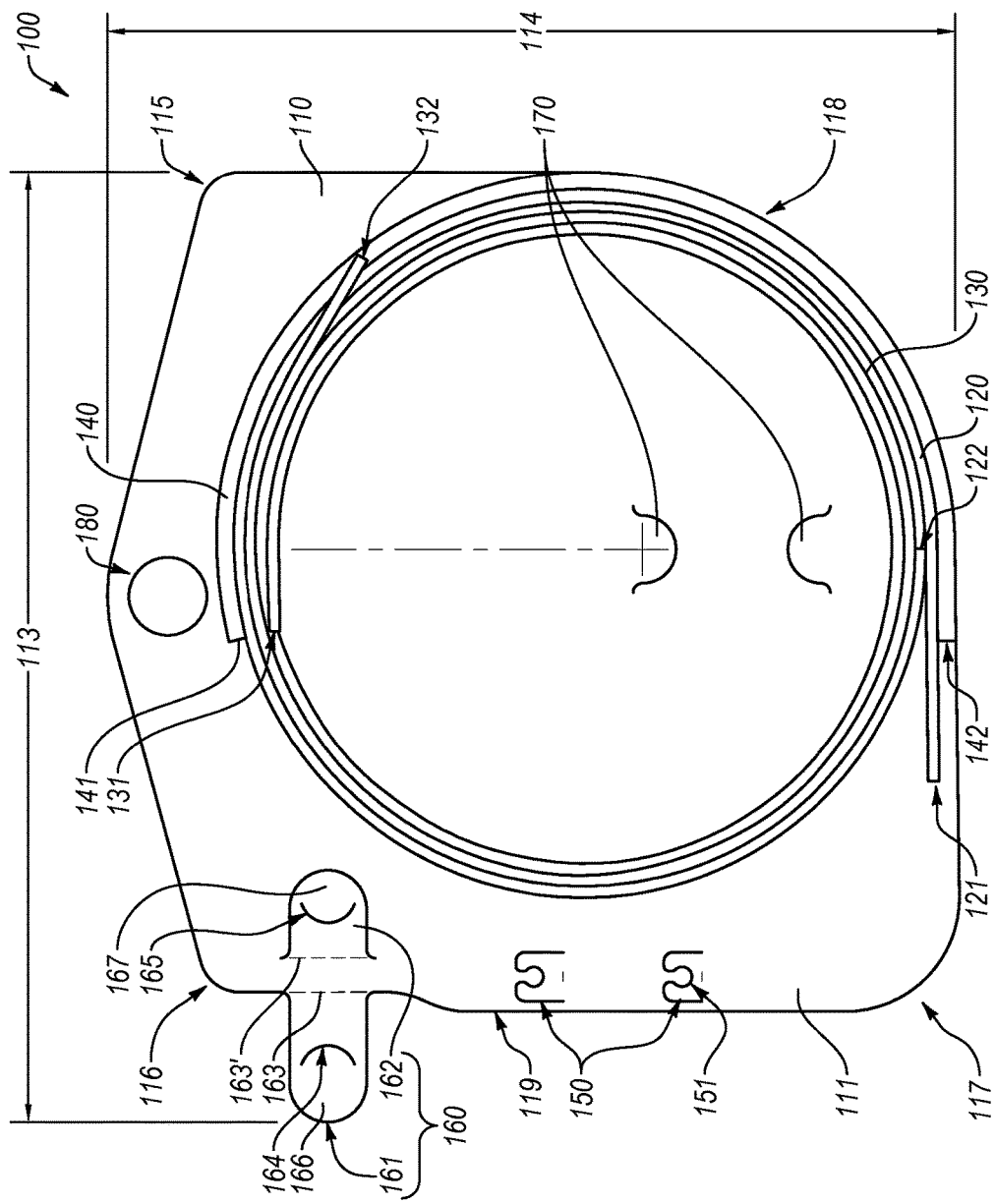
FIG. 1A is a top view of a urological kit packaging in accordance with an embodiment.
Figure 1B:
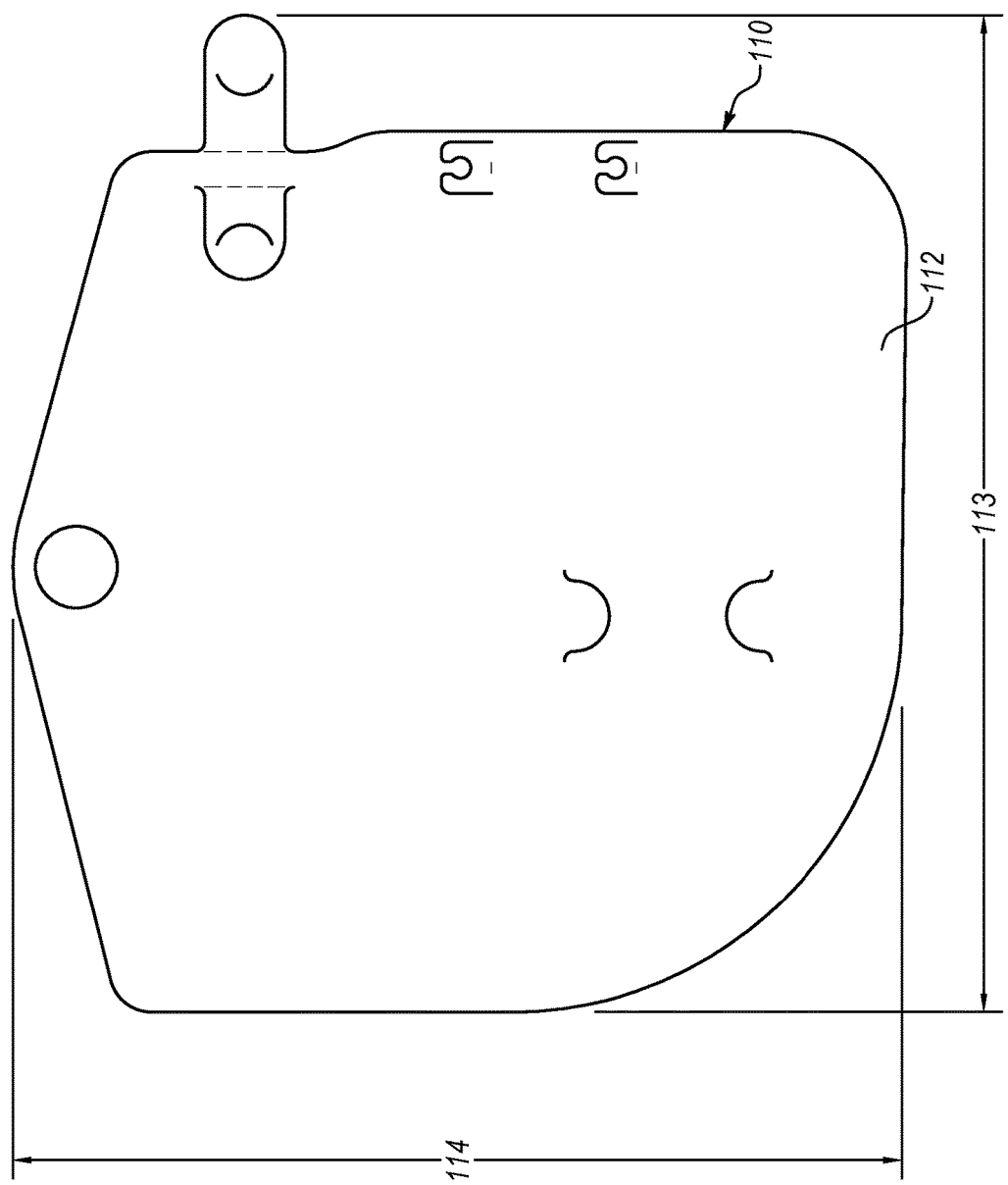
FIG. 1B is a bottom view of the urological kit packaging of FIG. 1A.

FIGS. 1A and 1B illustrate a urological kit packaging 100 that may secure one or more suitable urological devices, according to an embodiment. For example, the urological kit packaging 100 may include a base 110, which may secure one or more additional elements or components of the urological kit packaging 100. FIG. 1A is a top view of the urological kit packaging 100, such that a first major face 111 (e.g., top side) of the base 110 is visible; FIG. 1B is a bottom view of the urological kit packaging 100, such that a second, opposing major face 112 (e.g., back or bottom side) of the base 110 is visible.

Generally, the base 110 may be sufficiently rigid and/or resilient, such as to provide necessary or suitable support for the urological devices secured to the urological kit packaging 100. In some instances, the base 110 may be manufactured from a sheet- or plate-like material. In other words, the base 110 may be substantially two-dimensional, such that the thickness of the base 110 may be defined between the opposing first and second major faces 111, 112 (visible in FIGS. 1A, 1B, respectively) and may be substantially less than the widths and heights thereof.

It should be appreciated that the width and/or height of the first and second major faces 111, 112 (FIGS. 1A, 1B, respectively) and of the base 110 may vary from one embodiment to the next and may depend, among other things, on the particular urological procedure, urological devices secured to the urological kit packaging 100, etc. In an embodiment, as shown in FIG. 1A, the base 110 may have an overall width 113 of approximately 12 inches and a height 114 of approximately 11 inches. Similarly, the thickness of the base 110 may vary from one embodiment to the next and may depend on the particular material used to manufacture the base 110, the size of the base 110, etc. For instance, the base 110 may include high density polyethylene ("HDPE," e.g., recycled HDPE) and may have an approximate thickness of ⅛ inch. As noted above, however, the thickness of the base 110 may be less than ⅛ inch or greater than ⅛ inch. Likewise, the width 113 and the height 114 may be less or greater than 12 inches and 11 inches, respectively.

In some embodiments, the base 110 may include one or more rounded corners, such as rounded corners 115, 116, 117, 118, which may facilitate handling and/or storage of the urological kit packaging 100. For example, the rounded corners 115, 116, 117, 118 may reduce cuts or other injuries that may be otherwise caused by sharp corners formed between adjacent edges. Furthermore, the rounded corners 115, 116, 117, 118 may facilitate storage of the urological kit packaging 100 by reducing area or footprint thereof.

Alternatively or additionally, as described in further detail below, the urological kit packaging 100 may secure one or more elongated or cable-like urological devices (e.g., guidewire, stone removal basket, push catheter, access sheath assembly, laser fiber assembly, etc.). In some embodiments, the elongated urological devices may be at least partially looped or coiled and secured to and/or in the urological kit packaging 100. In at least one embodiment, the base 110 may include a rounded corner 118 that may approximately follow the radius of the coiled urological device(s).

In one or more embodiments, the urological kit packaging 100 may include one or more tubular members (e.g., tubular members 120, 130, 140), which may secure one or more elongated urological devices. For example, the tubular members 120, 130, 140 may be secured to the base 110 (e.g., on or near the first major face 111), and the elongated urological devices may be inserted into and stored within the tubular members 120, 130, 140. In particular, for example, each of the tubular members 120, 130, 140 may include a peripheral wall defining an internal space that may be sized and configured to accept and/or secure one or more urological devices therein. Accordingly, the tubular members 120, 130, 140 may secure the elongated urological devices to the base 110.

In one or more embodiments, the tubular members 120, 130, 140 may include material that may facilitate welding (e.g., ultrasonically welding) and/or adhering the tubular members 120, 130, 140 to the base 110 (e.g., on or near the first major face 111). For instance, the tubular members 120, 130, 140 may include or comprise a thermoplastic material. Additionally or alternatively, the tubular members 120, 130, 140 may be fastened to the base 110. In any event, the tubular members 120, 130, 140 may be suitably secured to the base 110.

In an embodiment, as shown in FIG. 1C, the base 110 may include an indication or a marking at a particular location for securing the tubular members 120, 130, 140 thereto. More specifically, in some instances, a mounting location 190 may be marked or otherwise indicated (e.g., recessed) on an appropriate side or face of the base 110, such as the first major face 111 of the base 110. Consequently, the tubular members 120, 130, 140 may be aligned to and secured to the base 110 at the mounting location 190. Moreover, in some embodiments, one or more of the tubular members 120, 130, 140 may be secured to each other. For instance, any of the tubular members 120, 130 and 140 may be secured or bonded to one another.

Referring again to FIG. 1A, in some 120, 130, 140, the tubular members 120, 130, 140 may be looped or coiled. Hence, inserting the elongated urological devices into the tubular members 120, 130, 140 may loop or coil the respective elongated urological devices. In at least one embodiment, coiling or looping the urological devices within the tubular members 120, 130, 140 may secure the respective elongated urological device within the tubular members 120, 130, 140 and to the base 110. Additionally or alternatively, the elongated urological devices may be secured to and/or within the tubular members 120, 130, 140 with adhesives, fasteners, or other suitable elements or components. Furthermore, in some embodiments, the elongated urological devices may have a snug or tight fit within the respective tubular members 120, 130, 140, which may restrict movement of the elongated urological devices within the tubular members 120, 130, 140.

It should be appreciated that, as described in further detail below, one or more of the elongated urological devices may be used by a user (e.g., a physician) during a urological procedure. Consequently, a user may remove any of the elongated urological devices from the respective tubular members 120, 130, 140. For example, the tubular members 120, 130, 140 may have one or more open ends (e.g., respective ends 121, 122, 131, 132, 141, 142) that may facilitate insertion of the elongated devices into the internal spaces of the tubular members 120, 130, 140 and/or removal of the elongated device therefrom. In some embodiments, however, at least one end of one or more of the tubular members 120, 130, 140 may be closed. For example, one or more of the tubular members 120, 130, 140 may include closed ends 122, 132, 142.

As described below in more detail, in an embodiment, a guidewire may be inserted into and secured within the internal space of the tubular member 130 and a portion of a stone removal basket may be inserted into and secured within the internal space of the tubular member 120. In some embodiments, a push catheter may be inserted into and/or secured within the internal space of the tubular member 140. In additional or alternative embodiments, the guidewire may be removed from the internal space of the tubular member 130 through or out of the open end 131 thereof during the urological procedure. Similarly, the push catheter may be removed from the internal space of the tubular member 140 through or out of the open end 141 thereof. In other words, while in the respective internal spaces, the tubular members 120, 130, 140 may secure one or more portions of elongated urological devices, the portion(s) of the elongated urological devices of the respective tubular member 120, 130, 140 may be movable or slidable in such internal spaces, such that the portions may be removed or withdrawn out of the tubular members 120, 130, 140 (e.g., without damaging the respective urological devices).

As described below, the stone removal basket may include a handle that may be secured to and/or positioned on the base 110 of the urological kit packaging 100 (e.g., on or near the first major face 111 of the base 110). More specifically, a proximal portion of the wire of the stone removal basket may attach to a distal portion of the handle of the stone removal basket. As such, in an embodiment, the proximal portion of the stone removal basket wire may extend from the open end 121 of the tubular member 120 and may be secured to the base 110 outside of the tubular member 120.

The urological kit packaging 100 also may include one or more elements, components, or features that may secure the handle of the stone removal basket. For example, the urological kit packaging 100 may include tabs 150 and/or tabs 160 (e.g., a first tab 161 and/or a second tab 162), which may be secured to and/or integrated with the base 110. In particular, in some embodiments, the tabs 150, 160 may secure the handle of the stone removal basket. In an embodiment, a proximal portion of the handle may be secured by and/or between the tabs 161, 162.

As described above, in some embodiments, the base 110 may be fabricated from sheet- or plate-like. For instance, the base 110 and/or one, some, or all of the tabs (e.g., tabs 150, 160, 170) may be cut, such as die cut, from a sheet of material, such as HDPE or similar material. In an embodiment, the urological kit packaging 100 may include cuts or slits extending into and/or through the sheet-like material of the base 110. For example, the tabs may be separated from the base 110 along the respective slits and may be bent away from the first major face 111 thereof (e.g., forming respective openings in the base 110 after being bent away therefrom). As shown in FIG. 1B, cuts or slits defining peripheral edges or perimeter of respective tabs may extend between the first major face and the second major face 112 and through the base 110.

Referring back to FIG. 1A, in one or more embodiments, the tabs 161, 162 may be bent and/or folded away from the first major face 111 and about at least a portion of the handle (e.g., to secure the proximal portion of the handle of the stone removal basket). For example, discussed below in more detail, the first and/or second tabs 161, 162 may at least partially wrap around the proximal portion of the handle. In some embodiments, the first tab 161 may protrude away from the first major face 111 (e.g., from an edge 119 that partially defines the perimeter of the first major face 111). Hence, in one or more embodiments, as described below in further detail, the first tab 161 may be folded about a fold line 163 toward the second tab 162. In an embodiment, the fold line 163 may approximately coincide or may be aligned with the edge 119 of the first major face 111 of the base 110.

In any event, in at least one embodiment, the first tab 161 and the second tab 162 (of the tabs 160) may be folded toward each other about one or more fold lines (e.g., about fold lines 163, 163') in a manner that secures the proximal portion of the handle therebetween. For instance, the first and/or second tabs 161, 162 may be plastically deformed at or near the fold line, such that the first and second tabs 161, 162 remain in a folded position and securing the proximal portion of the handle therebetween. Additionally or alternatively, the first and second tabs 161, 162 may attach or connect to each other and/or to the proximal portion of the handle, thereby securing the handle to the base 110.

For example, the tabs 161, 162 may include respective slits 164, 165 at least partially extending therethrough. In some embodiments, the slits 164, 165 may have generally arcuate shapes. The arcuate shapes of the slits 164, 165 may have opposing orientations to each other. In any event, the tabs 161, 162 may be partially separated or split along the slits 164, 165 into proximal portions and respective distal portions 166, 167. Moreover, as described below in more detail, when the tabs 161, 162 are folded together, the distal portion 167 of the tabs 162 may be inserted into the slit 164, thereby securing together the tabs 161, 162. It should be appreciated that the tabs 161, 162 may be secured together in any number of suitable ways and with any number of suitable mechanisms.

In some instances, the distal portion of the handle, which may connect to the wire of the stone removal basket, may be secured in the tabs 150. Alternatively or additionally, the base 110 as well as the tabs 150 and/or 160 may be molded or otherwise manufactured. In any event, for example, the tabs 150 may be cut out of the base 110 and may be bent or folded away from the first major face 111 in a manner that facilitates securing the distal portion of the handle of the stone removal basket (e.g., after bending, the tabs 150 may protrude or extend away from the top surface of the base 110).

In one or more embodiments, the tabs 150 may include snap-in or snap-over features that may secure the distal portion of the handle. For instance, the tabs 150 may include cutouts 151 that may be formed by opposing protrusions that may snap about the handle, thereby securing the handle to the tabs 150 and to the base 110. Moreover, the tabs 150 (e.g., cutouts 151 of the tabs 150) may removably secure the handle to the base 110. Hence, in at least one embodiment, the user may remove the handle from the urological kit packaging 100 (e.g., by pulling the handle out of the cutouts 151).

In some embodiments, the urological kit packaging 100 may include tabs 170 that may secure one or more urological devices to the base 110. For example, the tabs 170 may be cut out of the base 110 in the same or similar manner as the tabs 150. Accordingly, in at least one embodiment, the tabs 170 may be at least partially bent or folded out of the base 110 and away from the first major face 111. In some embodiments, the tabs 170 may be elastically bent outward away from the first major face 111 of the base 110 and may secure a urological device (e.g., by pressing the urological device against the top surface of the base 110). In other words, a urological device may be secured between the tabs 170 and the first major face 111 of the base 110 (e.g., positioning the urological device between the tabs 170 and the first major face 111 may bias the tabs 170, such that the tabs 170 press the urological device against the first major face 111).

In some embodiments, the urological kit packaging 100 may include an opening 180 (e.g., the base 110 may be perforated to form the opening 180 therein). For example, the opening 180 may accept a rod, a hook, or any other suitable element or device that may secure the urological kit packaging 100 during storage thereof. Furthermore, the opening 180 may facilitate transport of the urological kit packaging 100 (e.g., the user may carry the urological kit packaging 100 by grasping the urological kit packaging 100 through the opening 180).

Figure 2C:
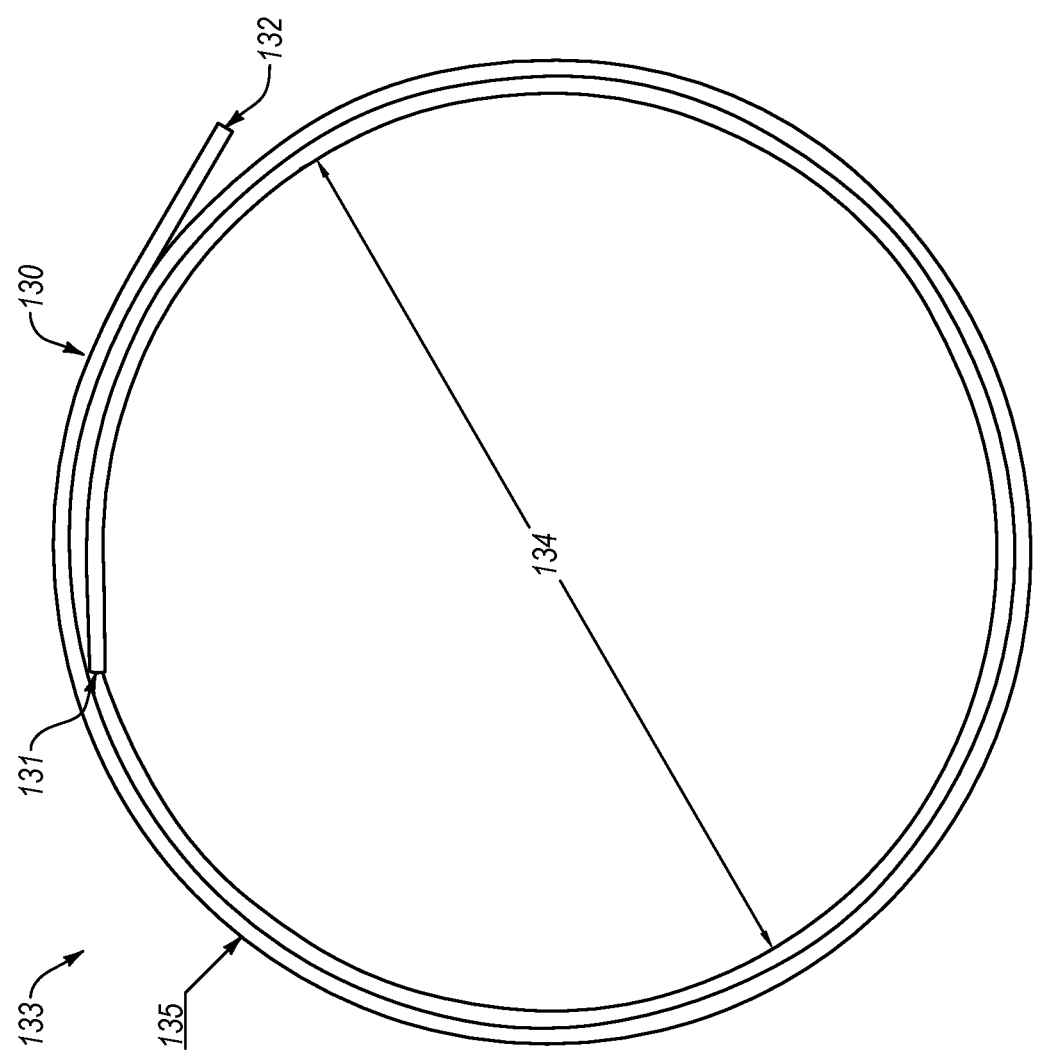
FIG. 2C is a top view of a coiled tubular member of a urological kit packaging for securing a urological device in accordance with an embodiment.

The particular sizes of the tabs and/or tubular members secured to and/or integrated with the base 110 may vary from one embodiment to another and may depend on the specific urological devices secured thereby. For example, as shown in FIGS. 2A-2C, sizes (i.e., diameters and/or lengths) of the tubular members 120, 130, 140 may vary one from another. FIG. 2A, for instance, illustrates the tubular members 120, 130 that may secure the wire of the stone removal basket therein, according to an embodiment. In an embodiment, the tubular member 120 may have an outside diameter (e.g., defined by an outer or peripheral surface of the tubular members 120, 130) in one or more of the following ranges: between about 0.05 inch and about 0.10 inch; between about 0.08 inch and about 0.15 inch; between about 0.13 inch and about 0.25 inch; between about 0.20 inch and about 0.40 inch (e.g., the outside diameter may be approximately 5/32 inch). In some instances, the outside diameter of the tubular member 120 may be less than 0.05 inch or greater than 0.40 inch. Similarly, the tubular member 120 may have an inside diameter (e.g., defined by interior surface that defines the internal space of the tubular member 120) in one or more of the following ranges: 0.03 inch and about 0.07 inch; between about 0.04 inch and about 0.09 inch; between about 0.05 inch and about 0.15 inch; between about 0.12 inch and about 0.25 inch; between about 0.20 inch and about 0.35 inch (e.g., the inside diameter may be an approximately 7/64 inch). It should be appreciated that the inside diameter of the tubular member 120 may be less than 0.03 or greater than 0.35 inch. In any event, the inside diameter of the tubular member 120 may facilitate insertion and storage of the wire of the stone removal basket.

Also, in some embodiments, the tubular members 120, 130 may have a length (e.g., defined between opposing open ends or between opposing open end and closed end) in one or more of the following ranges: between about 5 inches and about 15 inches; between about 10 inches and about 25 inches; between about 20 inches and about 40 inches; between about 30 inches and about 55 inches (e.g., the tubular members 120, 130 may have a length of approximately 31 inches). In some embodiments, the length of the tubular member 120 may be less than 5 inches or greater than 55 inches. As described above, the tubular members 120, 130 may be looped or coiled. In any event, the length of the tubular members 120, 130 may be suitable or sufficient to house the wire of the stone removal basket. In any event, the tubular members 120, 130 may have a suitable length and internal diameter to secure one or more urological devices as described herein.

In an embodiment, as shown in FIG. 2B, the tubular member 140 may have an inside diameter that is greater than the inside diameter of the tubular member 120, which may facilitate insertion and storage of the push catheter therein. In an embodiment, the tubular member 140 may have an outside diameter in one or more of the following ranges: between about 0.05 inch and about 0.10 inch; between about 0.08 inch and about 0.15 inch; between about 0.13 inch and about 0.25 inch; between about 0.20 inch and about 0.40 inch (e.g., the outside diameter may be approximately 7/32 inch). In some instances, the outside diameter of the tubular member 140 may be less than 0.05 inch or greater than 0.40 inch. Similarly, the tubular member 140 may have an inside diameter in one or more of the following ranges: 0.01 inch and about 0.07 inch; between about 0.04 inch and about 0.09 inch; between about 0.05 inch and about 0.15 inch; between about 0.12 inch and about 0.25 inch; between about 0.20 inch and about 0.35 inch (e.g., the inside diameter may be an approximately 11/64 inch). It should be appreciated that the inside diameter of the tubular member 140 may be less than 0.01 or greater than 0.35 inch.

Moreover, the tubular member 140 may have a length in one or more of the following ranges: between about 5 inches and about 15 inches; between about 10 inches and about 25 inches; between about 20 inches and about 40 inches; between about 30 inches and about 55 inches (e.g., the tubular member 140 may have a length of approximately 18 inches). In some embodiments, the length of the tubular member 140 may be less than 5 inches or greater than 55 inches. It should be appreciated that, however, any of the tubular members described herein may have any suitable length, internal dimension, external dimension, cross-sectional shape, or combinations thereof, which may vary from one embodiment to the next.

As described above, in some embodiments, one or more of the tubular members (e.g., tubular members 120, 130, 140 (FIG. 1A)) may be looped or coiled to facilitate storage of one or more urological devices. As shown in FIG. 2C, the tubular member 130 may be coiled to define a coil 133, according to an embodiment. For example, the coil 133 may have an inside diameter 134 (e.g., defined by a portion of the tubular member 130 that forms the innermost loop that may have a generally circular shape) by that may be in one or more of the following ranges: between about 1 inches and about 4 inches; between about 3 inches and about 8 inches; and between about 5 inches and about 15 inches (e.g., inside diameter of approximately 8 inches). Moreover, the coil 133 may have an outside diameter 135 (e.g., defined by a portion of the tubular member 130 that forms the outermost loop) in one or more of the following ranges: between about 1.2 inches and about 4 inches; between about 3.5 inches and about 7 inches; between about 5 inches and about 20 inches (e.g., an outside diameter of approximately 8 and three-quarter inches). In some embodiments, the coil formed by the tubular member 130 may have loops positioned in a single plane (e.g., spiraling away from the center of the coil). In other words, the tubular member 130 may coil such that portions thereof do not overlap one another.

It should be also appreciated that any of the tubular members described herein (e.g., tubular members 120, 130, 140 (FIG. 1A)) may be looped and/or coiled in any number of suitable configuration and/or may form or define any number of suitable shapes. For example, when looped or coiled, the tubular member 130 may define a coil having a generally elliptical shape, an irregular shape, etc. Moreover, when looped or coiled, the coil defined by the tubular members described herein (e.g., tubular member 130), one or more portions of the tubular member may extend over or may be positioned on top of one or more other portions of the tubular member.

In at least one embodiment, however, a portion of the tubular member 130 (e.g., a portion terminating at the open end 131) may overlap or lie on top of another portion of the tubular member 130. For example, the portion of the tubular member 130 that terminates at the open end 131 may define a portion of the inside diameter 134 of the coil 133. Furthermore, the portion of the tubular member 130 that defines the open end 131 thereof may extend out of the space defined by the inside diameter 134 of the coil 133 and over another portion of the tubular member 130. In any event, in some embodiments, the open end 131 may be positioned above or extend outward from the coil 133 and may be easily accessible. Hence, for example, the urological device (e.g., guidewire) located within the tubular member 130 may be pulled or otherwise removed from the open end 131 and over the outer surface of the tubular member 130 (e.g., surface defining the outside diameter of the tubular member 130).

Additionally or alternatively, one or more loops or portions of the coil 133 defined by the tubular member 130 may be secured or connected together (e.g., two or more portions of the tubular member 130 may be connected together, such as by gluing, welding, or otherwise connecting one portion of the tubular member 130 to another portion of the tubular member 130). For instance, the loops may be connected in a manner that prevents the tubular member 130 from unwinding. Accordingly, the coiled tubular member 130 may be secured or attached to the base as the coil 133 or in the coiled configuration (e.g., avoiding unwinding or uncoiling of the tubular member 130 on the base during attachment). It should be also appreciated that any of the tubular member described herein (e.g., the tubular members 120 and/or 140 (FIG. 1A)) may have similar coiled configurations and may be attached to the base in the same or similar manner as the tubular member 130.

Figure 3A:
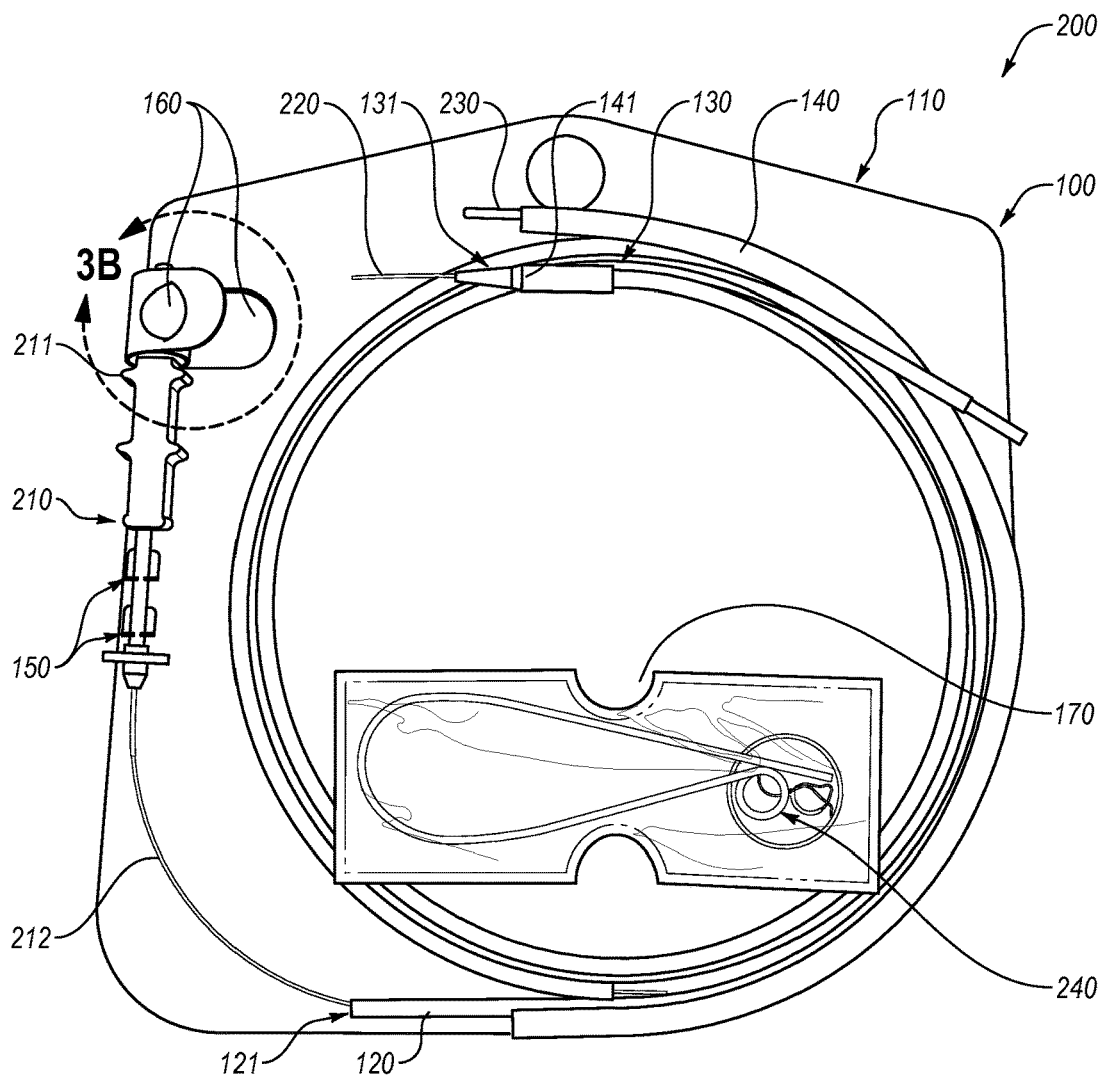
FIG. 3A is a urological kit in accordance with an embodiment.

FIG. 3A illustrates a urological kit 200 according to an embodiment. In particular, the urological kit 200 includes the urological kit packaging 100 and multiple urological devices secured by the urological kit packaging 100 according to one or more embodiments. In particular, for example, the urological kit 200 may include a stone removal basket 210 secured by and/or within the tubular member 120 as well as by the tabs 150 and 160.

For example, the stone removal basket 210 may include a handle 211 that may be secured by the tabs 150 and 160. In an embodiment, as described below in more detail, the tabs 160 may fold and/or wrap about or around the proximal portion of the handle 211, thereby securing the proximal portion of the handle 211 to the base 110 of the urological kit packaging 100. In some embodiments, as described above, the distal portion of the handle 211 may be snapped into the tabs 150, which may secure the distal portion of the handle 211.

Figure 3B:
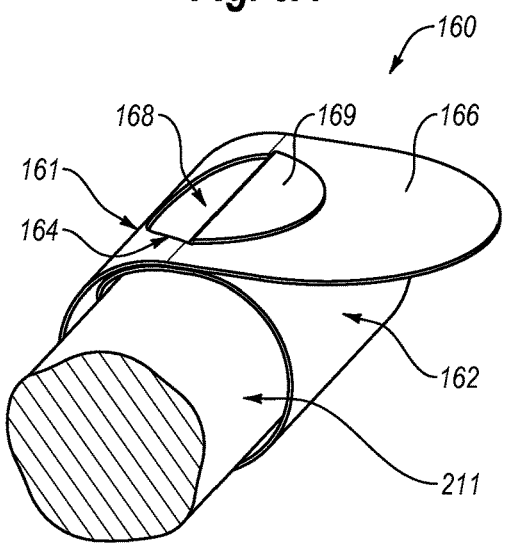
FIG. 3B is a partial isometric view of the urological kit of FIG. 3A.

FIG. 3B is an enlarged view of the tabs 160 securing the handle 211 that is only partially illustrated for convenience. For example, a portion of the first tab 161 may be bent or folded away from the slit 164, thereby forming an opening 168 in the distal portion 167 of the first tab 161. Moreover, a portion of the second tab 162 may be bent or folded away from the slit in the distal portion of the second tab 162, thereby defining a flap 169 on the second tab 162. The flap 169 may be inserted into the opening 168 and folded onto the distal portion 166 of the first tab 161 (e.g., onto a flap formed on the first tab 161, after folding away a portion of the first tab 161 from the slit 164 to form the opening 168).

In an embodiment, positioning the flap 169 of the second tab 162 in the opening 168 of the first tab 161 may connect together the first and second tabs 161, 162 and may wrap the first and second tabs 161, 162 about the handle 211 of the stone removal basket. To remove the handle 211 from the urological kit packaging, the flap 169 of the second tab 162 may be removed from the opening 168 of the first tab 161, thereby disconnecting the first and second tabs 161, 162 from each other and opening or providing access to remove the handle 211 therefrom.

Figure 3C:
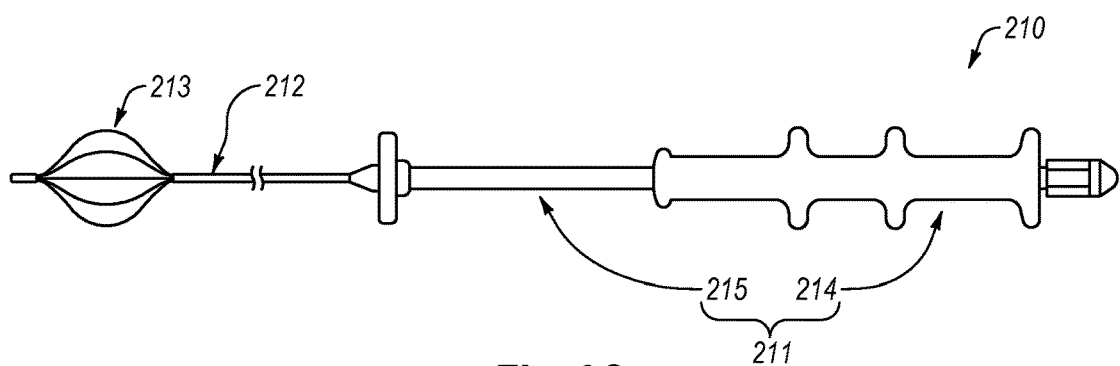
FIG. 3C is a top view of a urological stone removal basket included in the urological kit of FIG. 3A according to an embodiment.

Referring back to FIG. 3A, in some embodiments, the stone removal basket 210 includes a wire 212 that may be positioned and secured within the tubular member 120. As described above, the tubular member 120 may define or form a coil or a loop on the base 110. Hence, when inserted into the tubular member 120, the wire 220 may follow and/or conform to the looped or coiled shape of the tubular member 120. Moreover, the stone removal basket 210 may vary from one embodiment to the next. In one example, the stone removal basket 210 may be a BARD ECOFLEX stone removal basket (e.g., as schematically shown in FIG. 3C).

For a urological procedure, the handle 211 of the stone removal basket 210 may be removed or freed from the tabs 150, 160, and the wire 212 as well as the basket portion of the stone removal basket 210 may be withdrawn from the tubular member 120 (e.g., out of the open end 121 of the tubular member 120).

Additionally or alternatively, the urological kit 200 may include a guidewire 220 that may be position and secured within the tubular member 130 of the urological kit packaging 100. For example, the tubular member 130 may define or form a loop or a coil, and securing the guidewire 220 in the tubular member 130 may correspondingly loop or coil the guidewire 220. In an embodiment, a portion of the guidewire 220 may extend out of the open end 131 of the tubular member 130 (e.g., the guidewire 220 may have a greater length than the length of the tubular member 130). Hence, for example, for a urological procedure, the guidewire 220 may be removed or withdrawn from the tubular member 130 by pulling the guidewire 220 away from and out of the open end 131 of the tubular member 130. In an embodiment, the guidewire 220 may be a superelastic alloy guidewire (e.g., a nitinol guidewire such as a BARD NICORE guidewire). For example, the guidewire 220 may have a diameter between 0.035" and 0.038".

Furthermore, in some embodiments, the urological kit 200 may include a catheter, such as a push catheter 230, which and may be positioned and secured within the tubular member 140. As described above, the tubular member 140 may be looped or coiled. As such, for example, the push catheter 230 may be corresponding looped or coiled inside the tubular member 140. Moreover, in an embodiment, a portion of the push catheter 230 may extend out of the tubular member 140 (e.g., out of the open end 141 of the tubular member 140). During a urological procedure, for example, the push catheter may be withdrawn or removed from the tubular member 140 by pulling the push catheter 230 therefrom (e.g., away from and/or out of the open end 141 of the tubular member 140).

It should be appreciated that, generally, coiling the elongated portions of the urological devices may removably secure such portions in the corresponding tubular members. Additionally or alternatively, the elongated portion of the urological devices may be secured to and/or within the tubular members with adhesives, fasteners, press- or interference-fit, other suitable elements or components, or combinations of the foregoing. For example, the elongated portions of the urological devices may have a snug or tight fit within the respective tubular members such that the tubular members may restrict movement of the corresponding elongated portions of the urological devices.

Figure 3D:
FIG. 3D is a top view of a urological stent included in the urological kit of FIG. 3A, according to an embodiment.

As mentioned above, in some embodiments, one or more urological devices may be secured in the urological kit packaging 100 by one or more tabs. Moreover, such one or more urological devices may include generally elongated devices, which may also be secured within one or more corresponding tubular members. For example, the urological kit 200 may include a stent, such as a ureteral stent 240 that may be secured to the base 100 of the urological kit packaging 100 by the tabs 170. In an embodiment, the ureteral stent 240 may be a BARD INLAY™ ureteral stent (e.g., as schematically shown in FIG. 3D).

In some embodiments, the ureteral stent 240 may be prepackaged or sealed (e.g., in a plastic bag or container, or in an otherwise sterile environment) before the ureteral stent 240 is secured to the urological kit packaging 100. For example, the ureteral stent 240 together with the packaging may be secured between the base 110 and the tabs 170, as described above. Moreover, in at least one embodiment, the urological kit packaging 100 together with the stone removal basket 210, guidewire 220, push catheter 230, ureteral stent 240, or combinations thereof may be sterilized and/or sealed. For example, a plastic wrap or packaging may hermetically seal the urological kit packaging 100 therein.

As mentioned above, FIG. 3C schematically illustrates the stone removal basket 210. It should be appreciated that the stone removal basket may have any number of suitable configurations, which may vary from one embodiment to the next. In an embodiment, the stone removal basket 210 includes the handle 211 and the wire 212 extending from and attached to the handle 211. Generally, the wire 212 may terminate with and may be connected to a basket 213 (e.g., operation of the handle 211 may open and close the basket 213). For example, when the basket 213 is in a closed configuration, the outside dimension or outside diameter of the basket 213 may have the same or similar size as the outside dimension or diameter of the wire 212.

In an embodiment, at least a portion of the wire 212 may be positioned and secured in a tubular member of the urological kit packaging (e.g., in the tubular member 120 (FIG. 3A)). When the basket 213 is in a collapsed or closed configuration, at least a portion of the basket 213 may be positioned in the tubular member (e.g., in the tubular member 120 (FIG. 3A)). For example, the tubular member, such as the tubular member 120 (FIGS. 1A, 3A) may include an open end through which the wire 212 and the basket 213 may be inserted into the internal space of the tubular member 120, and an opposing closed end that at least partially seals or closes the internal space of the tubular member 120 and a portion of the wire 212 and the basket 213 therein. Alternatively, the basket 213 may be positioned outside of the tubular member (e.g., both ends of the tubular member may be open). As such, for example, the basket 213 may be opened and closed (e.g., to test operation thereof) without removing the wire 212 and the basket 213 from the tubular member.

Moreover, the handle 211 may include a proximal portion 214 and a distal portion 215. As described above, for example, the proximal portion 214 may be secured in the urological kit packaging 100 by and between the tabs 160 (FIGS. 3A-3B). In an embodiment, the distal portion 215 of the handle 211 may be secured in the urological kit packaging 100 by the tabs 150 (FIG. 3A), in a manner described above.

Again, FIG. 3D is a schematic illustration of the ureteral stent 240. Generally, the ureteral stent 240 may have an elongated configuration. In an embodiment, as described above, the ureteral stent 240 may be positioned and secured in a tubular member of a urological kit packaging. In some embodiments, additional or alternative urological devices may be included in the urological kit. For example, one, some, or all of the urological devices in the urological kit 200 may be substituted for a different urological device. In some embodiments however, the urological kit packaging may be configured to accommodate additional urological devices. For example, the urological kit packaging may include additional tubular members and/or tabs on or near the first major surface (e.g., near the top side of the base). Alternatively, as described below in more detail, the urological kit packaging may include one or more tabs and/or one or more tubular members on or extending away from a second major face (back side) of the base.

Figure 3E:
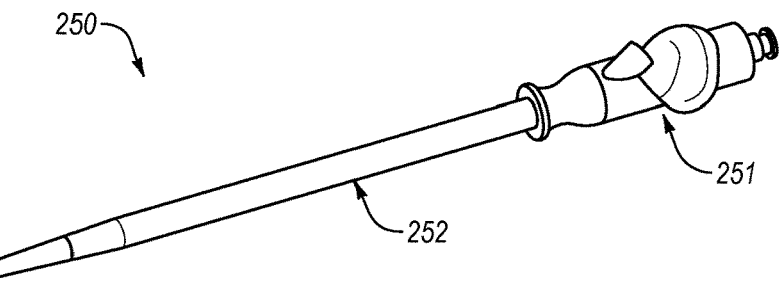
FIG. 3E is an isometric view of an access sheath assembly that may be included in a urological kit according to an embodiment.

In any event, in one or more embodiments, the urological kit may include an access sheath assembly 250, schematically illustrated in FIG. 3E, which may be secured within in the urological kit packaging by one or more tubular member and/or tabs, as described below. The access sheath assembly 250 may include a handle 251 and an access sheath 252 connected to the handle 251. Analogously, the access sheath 252 may be secured in a tubular member (e.g., in a manner described above in connection with the wire 212 of the stone removal basket 210 (FIG. 3A)).

The handle 251 may be secured in and/or by one or more tabs (e.g., as described above in connection with the handle 211 of the stone removal basket 210 (FIGS. 3A-3B)), the handle 251 may be secured by the tabs 150 and/or 160 (FIG. 1A). In an embodiment, the access sheath assembly 250 may be BARD AQUAGUIDE™. For example, the access sheath 252 may have a diameter between about 0.1 inch to about 0.2 inch and a length of about 10 inches to about 25 inches. Hence, for example, the tubular member(s) securing the access sheath 252 may have an inside dimension or diameter that is greater than 0.1 inch, such as to provide sufficient clearance for inserting and removing the access sheath 252.

Figure 3F:
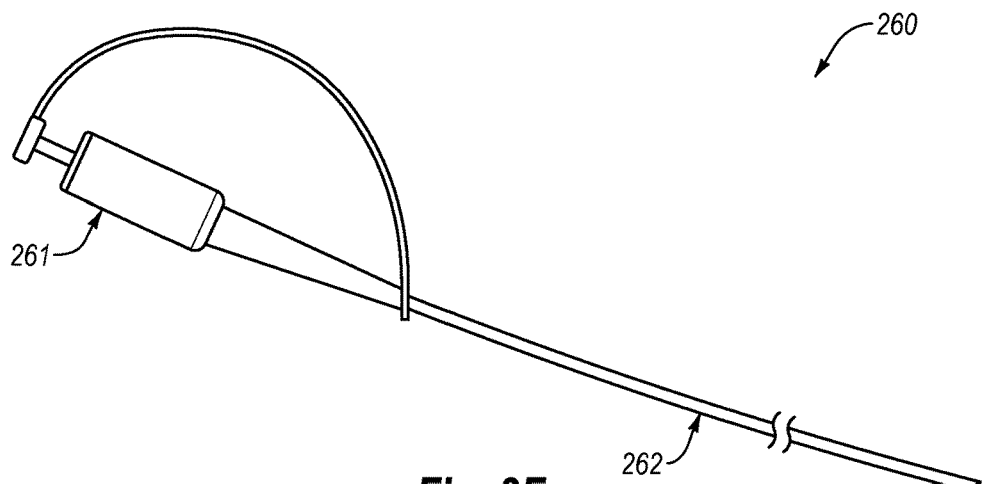
FIG. 3F is a top view of a laser fiber assembly that may be included in a urological kit according to an embodiment.

In some embodiments, the urological kit may include a laser fiber assembly 260, schematically illustrated in FIG. 3F, which may be secured in the urological kit packaging in and/or by one or more tubular members and/or tabs. The laser fiber assembly 260 may include an expansion knob or adapter 261 connected to a laser fiber 262. The laser fiber 262 may be secured by and/or in a tubular member (e.g., in a manner described above in connection with the wire 212 of the stone removal basket 210 (FIG. 3A)). Analogously, the adapter 261 may be secured in and/or by one or more tabs (e.g., as described above in connection with the handle 211 of the stone removal basket 210 (FIGS. 3A-3B)).

In an embodiment, the laser fiber assembly 260 may be a BARD ENDOBEAM™. Generally, the laser fiber may have any suitable length and/or diameter. For example, the laser fiber 262 may have a diameter between about 0.007 inch to about 0.05 inch and a length of about 5 inches to about 35 inches. Hence, for example, the tubular member(s) securing the access sheath 252 may have an inside dimension or diameter that is greater than 0.01 inch, such as to provide sufficient clearance for inserting and removing the access sheath 252.

In an embodiment, stone removal basket, guidewire, push catheter, ureteral stent, access sheath assembly, laser fiber assembly, or combinations thereof may alternatively or additionally be positioned and/or secured on or near a second major face or bottom side of the base. For example, the access sheath assembly 250 (FIG. 3E) and/or the laser fiber assembly (FIG. 3F) may be secured on or near the bottom face of the base in a similar or identical manner as the respective stone removal basket 210 may be secured to the first major face 111 or top side of the base 110 (FIG. 3A). Hence, in some embodiments, the ureteral kit may include stone removal basket, guidewire, push catheter, ureteral stent, access sheath assembly, laser fiber assembly, or any combination thereof positioned and/or secured on the top side and stone removal basket, guidewire, push catheter, ureteral stent, access sheath assembly, laser fiber assembly, or any combination thereof secured on the bottom side of the base.

Figure 4A:
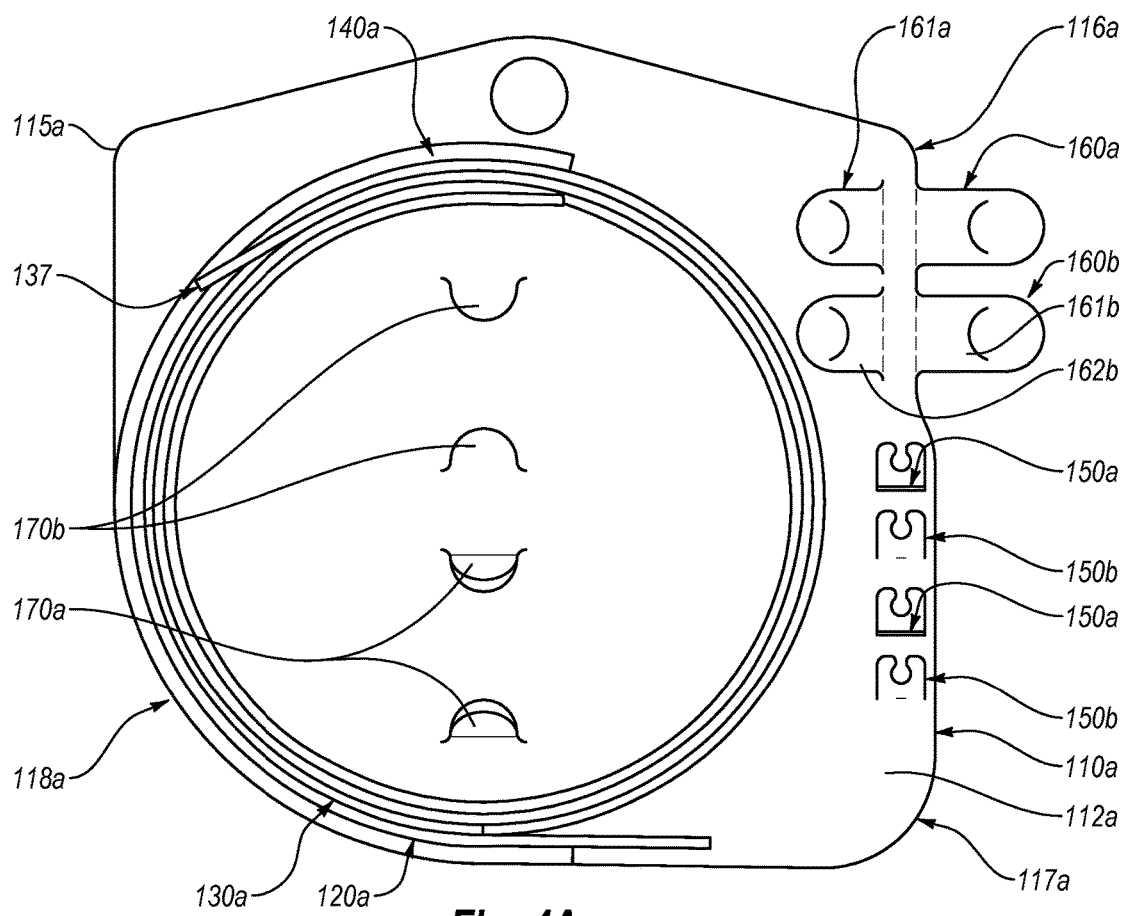
FIG. 4A is a bottom view of a urological kit packaging in accordance with an embodiment.

In any event, in some embodiments the urological kit packaging may be configured to secure one or more urological device only the top side of the base (e.g., on the first major face), while in additional or alternative embodiments, the urological kit packaging may be configured to secure one or more urological devices on the bottom side of the base (e.g., on the second major face). FIG. 4A is a bottom view of a urological kit packaging 100a that is configured to secure urological devices on top and bottom sides thereof, according to an embodiment. For example, FIG. 4A shows a bottom side or a second major face 112a of the urological kit packaging 100a. Except as described herein, the urological kit packaging 100a and its elements and components may be similar to or the same as the urological kit packaging 100 (FIGS. 1A-1B) and its corresponding elements and components. For example, the urological kit packaging 100a may have a top side or first major face thereof (not visible) configured in a similar or the same manner (e.g., to include the same or similar tubular members and/or tabs, which may be positioned at the same or similar locations) as the first major face 111 of the urological kit packaging 100 (FIG. 1A).

Figure 4B:
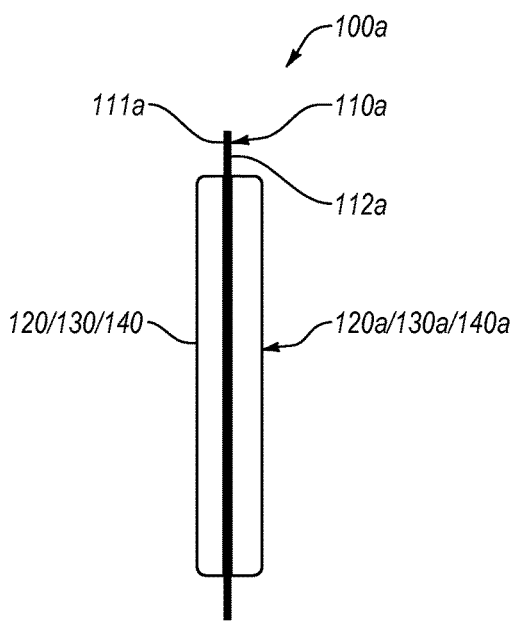
FIG. 4B is a side view of the urological kit packaging of FIG. 4A.

The urological kit packaging 100a may include one or more tubular members and/or one or more tabs secured to and/or extending from the second major face 112a. In the illustrated example, the urological kit 100a includes tubular members 120a, 130a, 140a. The tubular members 120a, 130a, 140a may be the same as or similar to the tubular members 120, 130, 140 (FIG. 1A). In an embodiment, position(s) and/or attachment of one or more of the tubular members 120a, 130a, 140a relative to the second major face 112a of the base 110a may be the same as or similar to the position(s) and/or attachment of the tubular members 120, 130, 140 relative to the first major face of the base (FIGS. 1A, 4B). In an embodiment, the tubular members 120a, 130a, 140a may be secured to the second major face 112a.

As shown in FIG. 4B, in at least one embodiment, the tubular members 120, 130, 140 may be positioned on and secured near first major face 111a of the base 110a (e.g., in the same or similar manner as the tubular members 120, 130, 140 may be positioned on and secured near the first major face 111 of the base 110 (FIG. 1A)). As described above, the tubular members 120a, 130a, 140a may be positioned on and secured near the second major face 112a of the base 110a. Any of the tubular members 120, 120a, 130, 130a, 140, or 140a may contain any of the elongated urological devices disclosed herein. In embodiments utilizing both sides of the base (e.g., of the base 110a), the urological kit packaging 100a may facilitate including additional and/or alternative urological devices in the urological kit packaging (as compared with a single-sided urological kit packaging), which may reduce the number of urological kits and/or kit packaging units storing urological devices. Moreover, in some embodiments, the duration of the urological procedure may be shortened due to the centralization of the required urological device to one base.

Referring again to FIG. 4A, in one or more embodiments, the urological kit packaging 100a may include tabs 150a, 160a, 170a, or combinations thereof, which may be similar to or the same as the tabs 150, 160, 170 of the urological kit packaging 100 (FIG. 1A). For example, the tabs 150a, 160a, 170a may be positioned on or near the first major face 111a of the base 110 and may have the same or similar relative positions as the tabs 150, 160, 170 of the urological kit packaging 100 (FIG. 1A). For example, the tabs 160a may be bent away from the base 110a and outward from the first major face thereof (e.g., folding one of the tabs 160a may form an opening the base 110a at least partially defined by slit 161a).

For example, the tabs 160a may be folded together about a portion of a urological device (e.g., about the handle of a stone removal basket) to secure that at least portion of the urological device at or near the first major face 111a (FIG. 4B). Alternatively, one, some, or all of the tabs 150a, 160a, 170a may be folded or bent away from the base 110a such as to extend outward from the second major face 112a of the base 110a. As such, one, some, or all of the tabs 150a, 160a, 170a may secure one or more urological devices or portion(s) thereof on or near the second major face 112a. For example, the tabs 160a may be bent to extend away from the second major face 112a of the base 110a and/or toward about a portion of the urological device (e.g., a portion of a handle of a urological device), such as to secure the urological device or a portion thereof at or near the second major face 112a.

Moreover, one, some, or all of the tabs may include snap-over features that may secure a portion of a urological device (e.g., a distal portion of a handle of a urological device). For instance, the tabs 150a may include cutouts (similar to cutouts 151 of tabs 150 (FIG. 1A)), which may removably secure the handle to the base 110a (e.g., on the top side or the first major face 111a (FIG. 4B) of the base 110a). In other words, the tabs 150a may be bent away from the base 110a and outward from the first major face of the base 110a (e.g., thereby forming openings in the base 110a). Alternatively, the tabs 150a may be bent to extend outward from the second major face 112a, such that a portion of the urological device secured thereby may be positioned near the second major face 112a.

The tabs 170a may be cut out of the base 110a in the same or similar manner as the tabs 170 (FIG. 1A). In some embodiments, the tabs 170a may be at least partially bent or folded out of the base 110a, such as to extend outward from the first major face or from the second major face 112a. For example, a urological device may be secured between the tabs 170a and the first major face or between the tabs 170a and the second major face 112a of the base 110a.

In some embodiments, the base 110 may include more than one set of tabs, such that some tabs may extend outward from the first major face 111a (FIG. 4B), and other tabs may extend outward from the second major face 112a. For example, the urological kit packaging 100a may include tabs 150b, 160b, 170b, or combinations thereof, which may extend outward from the second major face 112a of the base 110a. The tabs 150b, 160b, 170b may be similar to or the same as the tabs 150a, 160a, 170a. For example, the tabs 160b may include tabs 161b, 162b that may bend or fold together and away from the second major face 112a of the base 110a, securing at least a portion of a urological device (e.g., the handle 251 of access sheath assembly 250 (FIG. 3E), the adapter 261 of the laser fiber assembly 260 (FIG. 3F), etc.).

Additionally or alternatively, the tabs 150b, 160b, 170b may bend in a similar manner (but in some embodiments, in an opposing direction) as the tabs 150a, 160a, 170a. As such, the urological kit packaging may position and/or secure any suitable urological devices on or near the first and/or the second major faces 111a (FIG. 4B), 112a. It should be appreciated, however, that any of the tabs 150a, 150b, 160a, 160b, 170a, 170b may be bent or folded to extend outward from the first major face 111a (FIG. 4B) or from the second major face 112a (e.g., to secure one or more portions of urological device(s) to or near the corresponding first and/or the second major faces 111a (FIG. 4B), 112a).

In some instances, the tabs 150a and 150b, 160a and 160b, 170a and 170b may be offset or distanced one from another, such as not to interfere with one another (e.g., during use). For example, the tabs 150a and 150b, 160a and 160b, 170a and 170b may be offset from each other along the same direction. Alternatively, the tabs 150a and 150b, 160a and 160b, 170a and 170b may be offset from each other along multiple directions. In any event, in some embodiments, the urological kit packaging 100 may include tabs 150a, 160a folded toward or onto the first major face 111a (FIG. 4B) and tabs 150b, 160b may be folded toward or onto the second major face 112a.

As described above, any number of the urological devices (e.g., urological devices described herein) may be secured in the urological kit packaging 100a and near the first major face 111a (FIG. 4B) or near the second major face 112a. For example, the handle 211 of the stone removal basket 210 (FIG. 3A) may be secured in and by the tabs 150a, 160a near the first major face 111a (FIG. 4B) of the urological kit packaging 100a. Analogously, the wire 212 and/or the basket 213 of the stone removal basket 210 (FIG. 3A) may be positioned in a tubular member on the first major face 111a, such as in the tubular member 120a (FIG. 4B). In an embodiment, the guidewire 220 (FIG. 3A) may be secured in the tubular member 130a and near the first major face 111a (FIG. 4B). Also as described above, the ureteral stent 240 (FIG. 3A) may be secured between the tabs 170a and the first major face 111a of the urological kit packaging 100a (FIG. 4B).

As mentioned above, in some embodiments, an access sheath assembly (e.g., the access sheath assembly 250 (FIG. 3E)) may be positioned or secured near the second major face 112a of the base 110a. For example, the handle 251 of the access sheath assembly 250 (FIG. 3E) may be secured near the second major face 112a by the tabs 150b, 160b, and the access sheath 252 of the access sheath assembly 250 (FIG. 3E) may be secured near the second major face 112a by and within the tubular member 120a. In an embodiment, a laser fiber assembly (e.g., the laser fiber assembly 260 (FIG. 3F)) may be positioned near the second major face 112a of the base 110a. For example, the laser fiber (e.g., laser fiber 262 (FIG. 3F)) may be positioned in a tubular member (e.g., in the tubular member 130a) in a manner that secures the laser fiber assembly in the tubular member. It should be appreciated that any of the urological devices described herein may be secured near the first and/or second major faces 111a (FIG. 4B), 112a of the base 110a as well as by and/or within any of the tubular members and tabs described herein. Moreover, any number of tubular members may be positioned on or near the first and/or second major faces 111a (FIG. 4B), 112a of the base 110a. As such, any number of urological devices may be secured within the tubular member near the first major face 111a (FIG. 4B), and any number of urological devices may be secured within the tubular member near the second major face 112a.

Figure 5A:
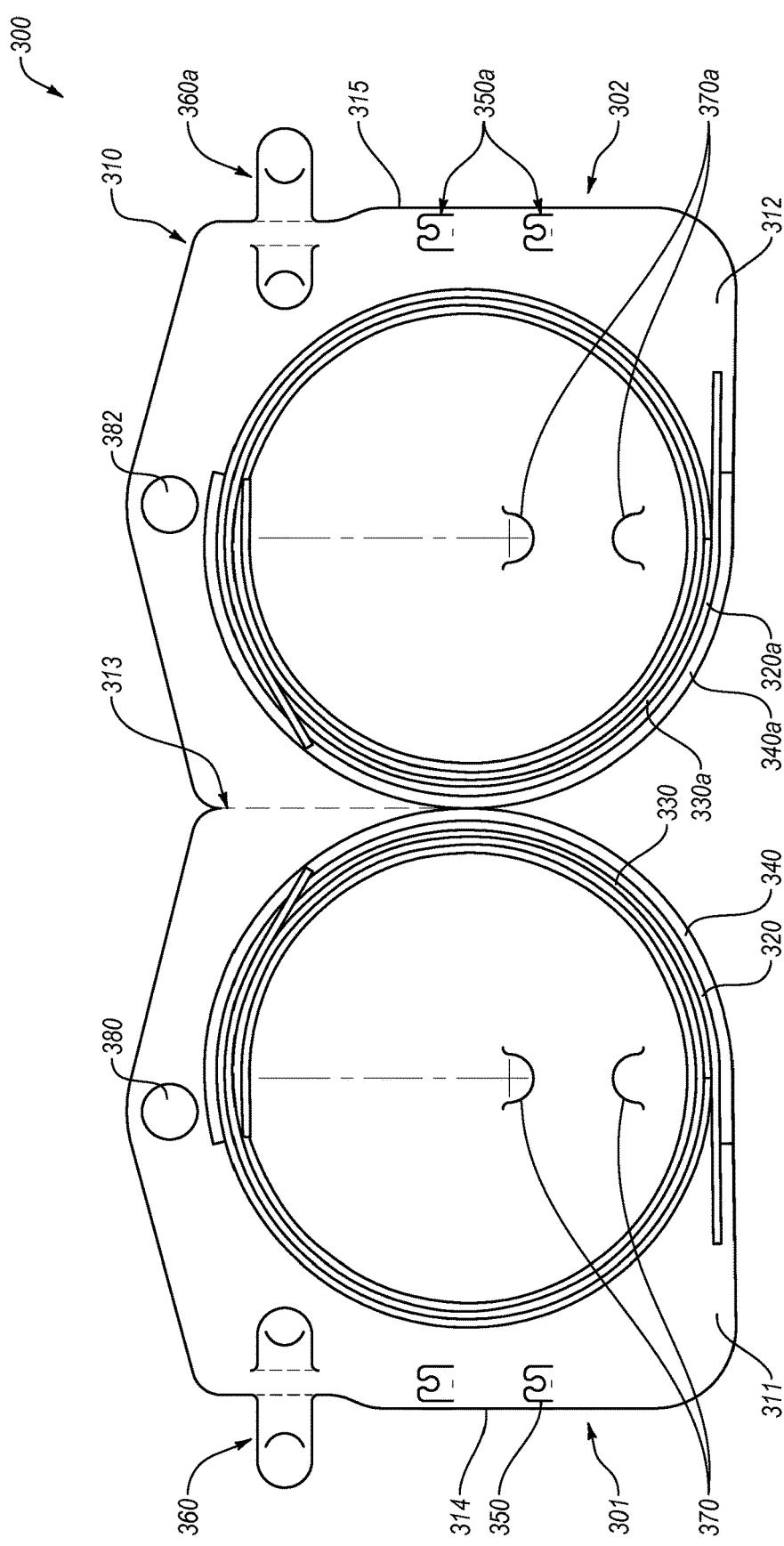
FIG. 5A is a top view of a urological kit packaging in accordance with another embodiment.

In some embodiments, the urological kit packaging may be configured such that the urological devices positioned and/or secured near the first and second major faces thereof may be oriented to face in the same direction (e.g., to face a user, such as during the urological procedure). For example, the first and second major faces may be arranged side-by-side relative to each other, such that the urological devices positioned and/or secured near the first and second major faces may be oriented to face in the same direction (e.g., during use). FIG. 5A is a top view of a urological kit packaging 300 that includes a foldable base 310, which has first and second major faces 311, 312 that may be oriented to face in the same direction, according to an embodiment.

Except as otherwise described herein, the urological kit packaging 300 and its elements and components may be similar to or the same as any of the urological kit paging units 100, 100a (FIGS. 1A-1C, 4A-4B) and their corresponding elements and components. For example, the foldable base 310 may be made from the same or similar materials and/or may have the same or similar thickness as the base 110 (FIGS. 1A-1C). As described above, the foldable base 310 may include first and second major faces 311, 312, which may be defined by or located on corresponding first and second sides 301, 302. In an embodiment, the first and second sides 301, 302 may be foldable or pivotably connected together (e.g., such that the first side 301 may be folded toward and/or onto the second side 302 and vice versa).

In an embodiment, the first and second major faces 311, 312 may be located on corresponding first and second sides 301, 302 of the foldable base 310. Moreover, one, some, or each of the first and second sides 301, 302 of the foldable base 310 may be configured to be similar to or the same as any of the urological kit packaging units 100, 100a (FIGS. 1A-1C, 4A-4B). In other words, for example, the first major face 311 of the foldable base 310 may be similar to or the same as the first major face 111 of the urological kit packaging 100 (FIG. 1A), and the second major face 312 of the foldable base 310 may be similar to or the same as the first major face 111a of the urological kit packaging 100a (FIG. 4A). Hence, any number of corresponding urological devices may be secured in the urological kit packaging 300 (e.g., in a similar manners as described above in connection with the respective first major face 111 of the urological kit packaging 100 (FIG. 1A) as well as the first and/or second major faces 111a, 112a of the urological kit packaging 100a (FIG. 4A-4B)).

In an embodiment, the foldable base 310 may include multiple pieces of material joined together and having a fold line 313 therein and/or therebetween. For example, the fold line 313 may be located between and define the separation between the first major face 311 and the second major face 312. Additionally or alternatively, the fold line 313 may be formed in and/or located on a single piece of material. Moreover, in an embodiment, the fold line 313 may be located equidistantly or non-equidistantly between a first edge 314 and a second edge 315 of the respective first and second sides 301, 302 of the foldable base 310. The fold line 313 may include or may be defined by a crease, perforations, or one or more similar features formed in the material of the foldable base 310, which may facilitate folding together the first and second sides 301, 302. In alternative or additional embodiments, the fold line may be formed at or defined by a member configured to fold (e.g., a hinge) to facilitate folding together the first and second sides 301, 302.

In some embodiments, one, some, or each of the features, elements, or components of the first side 301 and/or of the first major face 311 may have a mirrored positioned and/or orientation about the fold line 313 relative to corresponding features, elements, or components of the second side 302 and/or of the second major face 312. For example, the perimeter or peripheral shape of the first and second major faces 311, 312 may be at least partially defined by one or more radii (e.g., as described above in connection with urological kit packaging 100 (FIG. 1A)). In an embodiment, radii of the first major face 311 may have a mirrored position and orientation about the fold line 313 relative to the radii of the second major face 312. As such, for example, the first and second sides 301, 302 may be folded together about the fold line 313, such that the corresponding radii thereof generally align with each other. In an embodiment, the opposing first and second sides 301, 302 may include corresponding openings 380, 382. When the first and second sides 301, 302 are folded together, the openings 380, 382 may be aligned with each other, such as to allow placement of an element or component (e.g., a storage hook or a package fastener) therethrough.

Similar to the urological kit packaging 100 (FIG. 1A), the urological kit packaging 300 may secure one or more elongated and/or cable-like urological devices (e.g., guide-wire, stone removal basket, push catheter, access sheath assembly, laser fiber assembly, etc.). In one or more embodiments, the urological kit packaging 300 may include one or more tubular members (e.g., tubular members 320, 325, 330, 335, 340, 345), which may secure one or more elongated urological devices. Generally, the tubular members 320, 320a, 330, 330a, 340, 340a may be similar to or the same as the corresponding tubular members 120, 120a, 130, 130a, 140, 140a (FIGS. 1A, 4A).

For example, the tubular members 320, 330, 340 may be secured to the first side 301 of the foldable base 310 (e.g., on or near the first major face 311). In some embodiments, one or more elongated urological devices may be at least partially inserted into and stored within respective the tubular members 320, 330, 340. Analogously, the tubular members 320a, 330a, 340a may be secured on the second side 302 of the foldable base 310 (e.g., on or near the second major face 312). In one or more embodiments, and the tubular members 320a, 330a, 340a may contain and/or secure one or more respective urological devices therein. Accordingly, for instance, the tubular members 320, 330, 340 may secure one or more elongated urological devices on the first side 301 of the foldable base 310 (e.g., on or near the first major face 311), and the tubular members 320a, 330a, 340a may secure one or more additional or alternative urological devices on the second side 302 of the foldable base 310 (e.g., on or near the second major face 312).

In some embodiments, attachment of the tubular members 320, 320a, 330, 330a, 340, 340a to the foldable base 310 (e.g., on or near first and/or second major faces 311, 312 of the respective first and second sides 301, 302) may be the same as or similar to the attachment of the tubular members 120, 120a, 130, 130a, 140, 140a to the base 110a (FIGS. 4A-4B), as described above. For example, the tubular members 320, 320a, 330, 330a, 340, 340a may include material that may facilitate welding (e.g., ultrasonically welding) and/or adhering the tubular members 320, 330, 340 to the foldable base 310.

In some embodiments, one, some, or each of the tubular members 320, 320a, 330, 330a, 340, 340a may be looped and/or coiled as described above in connection with the tubular members 120, 130, 140 (FIGS. 1A-2C). For instance, coiling or looping the urological devices within any of the tubular members 320, 320a, 330, 330a, 340, 340a, which may be cause by the looped and/or coiled shape(s) of the tubular members, may secure the urological device within the respective tubular member 320, 320a, 330, 330a, 340, 340a.

In some embodiments the urological kit packaging 300 may include one or more tabs, such as tabs 350, 360, 370, 350a, 360a, 370a. The tabs 350, 360, 370, 350a, 360a, 370a may be the same as or similar to the corresponding tabs 150, 160, 170, 150a, 160a, 170a (FIGS. 1A, 4A). For example, the first side 301 may include tabs 350, 360, 370, wherein the tabs may be positioned in an identical or different position on the foldable base 310 than described above with respect to tabs 150, 160, 170 (FIG. 1A). In an embodiment, the second side 302 may include one or more tabs 350a, 360a, 370a, which may be positioned at the same or different locations on the foldable base 310 as described above in connection with the tabs 150a, 160a, 170a (4A). For example, the first side 301 may include tabs 350, 360 370, and the second side 302 may include tabs 350a, 360a, 370a, such that when the first and second sides 301, 302 of the foldable base 310 are folded together (e.g., along the fold line 313), one or more of the tabs 350, 360, 370 on the first side 301 and one or more of the tabs 350a, 360a, 370a on the second side 302 may substantially align.

In an embodiment, one or more of the tabs 350, 360, 370, 350a, 360a, 370a on opposing sides may be configured to interlock or connect together when the first side 301 is folded toward or onto the second side 302. For example, the one or more of the tabs 350, 360, 370 on the first side 301 may connect to or interlock with one or more of the tabs 350a, 360a, 370a on the second side 302 and may keep or retain the foldable base 310 in the folded configuration. Alternatively or additionally, each of the first side 301 or the second side 302 may include an attachment member suitable to affix or secure a counterpart attachment feature on the opposite side, such as to retain or affix the foldable base 310 in the folded configuration. For example, suitable attachment features include one or more tabs, one or more hook and loop fasteners, one or more snaps, one or more magnets, combinations of the foregoing, etc. In an embodiment, the tabs 350, 360, 370, 350a, 360a, 370a on the respective first and second sides 301, 302 may be positioned and configured such that one or more of the tabs 350, 360, 370, 350a, 360a, 370a may not align with another of corresponding tabs 350, 360, 370 350a, 360a, 370a (e.g., when the first and second sides 301, 302 are folded together).

The width and/or height of the foldable base 310 may vary from one embodiment to the next and, among other things, may depend on the type and number of urological devices stored thereon. In some embodiments, the total width (e.g., defined by the sum of the widths of the first and second major faces 311, 312) of the foldable base 310 may be substantially larger than the height of the foldable base 310. For example, the foldable base may have a width of about 24 inches and height of about 11 inches, such that when the foldable base 310 is folded (e.g., along the fold line 313) the width of the folded urological kit packaging 300 is about 12 inches.

As mentioned above, the first and second sides 301, 302 may be folded toward each other, such as by elastic and/or plastic deformation of the foldable base 310 along or near the fold line 313. Folding of the foldable base 310 may result in the foldable base 310 permanently or reversibly remaining in a folded position. Moreover, in some embodiments, when the foldable base 310 is folded, the first and second major faces 311, 312 may generally face or oppose each other and may be biased away or toward each other (e.g., a retainer may hold the base 310 folded, and removal of the retainer may allow the first and second sides 301, 302 to flex away from each other, thereby unfolding the base 310).

Figure 5B:
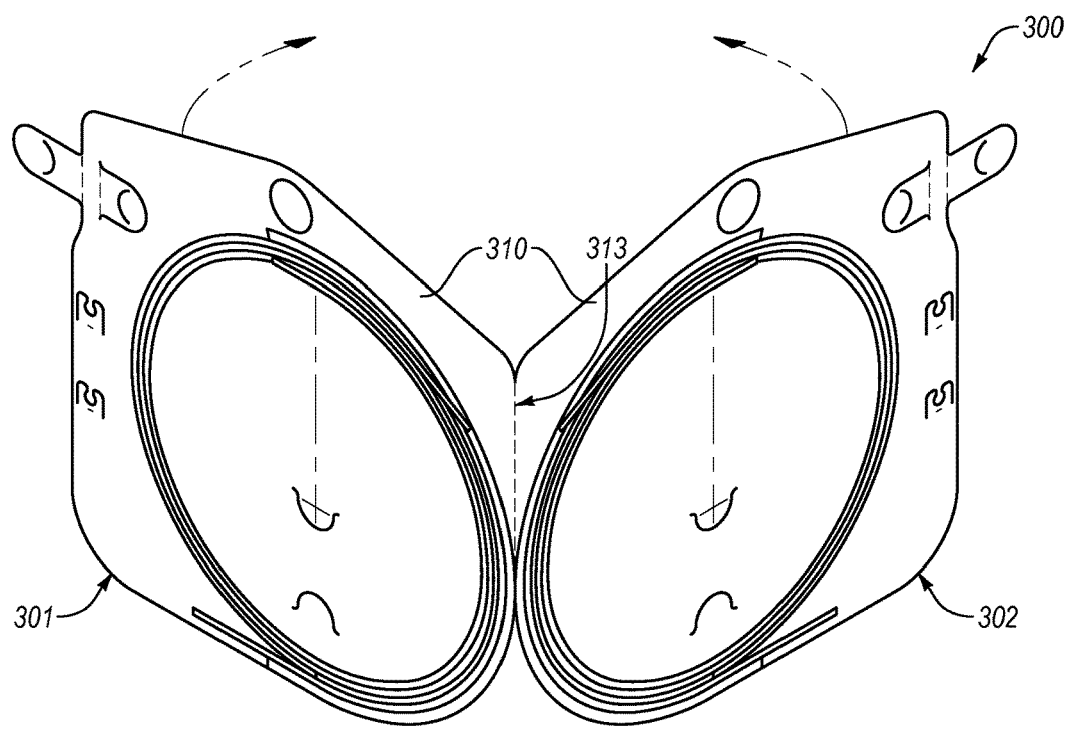
FIG. 5B is an isometric view of the urological kit packaging of FIG. 5A partially folded according to an embodiment.

As shown in FIG. 5B, the foldable base 310 may be folded along the fold line 313, such that the first side 301 and second side 302 face away from each other, according to an embodiment. For example, the first and second sides 301, 302 may abut each other (e.g., the foldable base 310 may fold to a back-to-back configuration). Such folded configuration may facilitate visibility of some or all of the urological devices stored in the urological kit packaging 300.

Figure 5C:
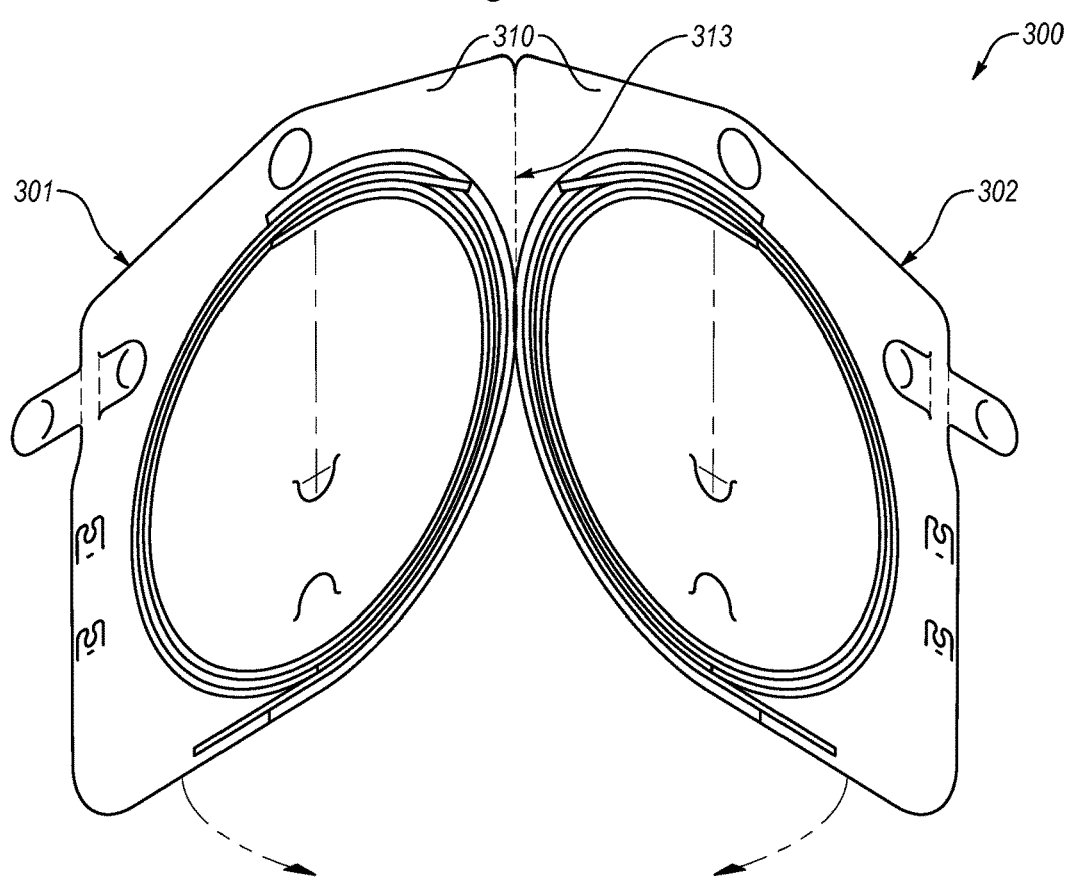
FIG. 5C is an isometric view of the urological kit packaging of FIG. 5A partially folded according to another embodiment.

Alternatively, as shown in FIG. 5C, the foldable base 310 may be folded along the fold line 313 such that the first side 301 and second side 302 face each other, according to at least one embodiment. For example, the first and second major faces may be reoriented to face each other and/or may be positioned near each other (e.g., the foldable base 310 may be folded to a face-to-face configuration). As such, for example, the outward facing major faces (which oppose first and second major faces) of the foldable base 310 may protect the contents of the urological kit packaging 300 from damage. In an embodiment, the urological kit packaging 300 may unfold along the fold line 313 such that all of the urological devices or tools thereon face upward (e.g., all of the urological device may face the user when the urological kit packaging 300 is unfolded). Moreover, as discussed above, in an embodiment, the urological kit packaging 300 or portions thereof together with urological devices secured thereby may be placed and/or sealed in a sterile bag or other container suitable to provide sterile environment therefor.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A packaging for a urological kit, the package comprising:
    a base having generally opposing first and second major faces defining a thickness of the base by a distance therebetween, the base having a width and a height that are substantially greater than the thickness thereof;
    one or more tubular members including a first tubular member, the one or more tubular members secured to the first major face of the base, at least the first tubular member of the one or more tubular members having a coiled configuration with loops thereof located generally in a single plane, a portion of the first tubular member terminating at an open end and extending out of the single plane and over another portion of the first tubular member, each of the one or more tubular members defining an internal space sized and configured to secure one or more first urological devices;
    a second tubular member having a looped or coiled configuration having loops thereof located in the single plane, a portion of the second tubular member terminating at an open end and extending out of the single plane and over another portion of the second tubular member;
    and one or more tabs secured to or integrated with the base, the one or more tabs being sized and configured to wrap about at least a portion of at least one of the one or more first urological devices or one or more second urological devices.

2. The packaging of claim 1 wherein the first major face of the base includes a sheet material that defines the first and second major face and includes an indication of an identified mounting location for the one or more tubular members, and the one or more tubular members are secured to or integrated with the base at the mounting location.

3. The packaging kit of claim 2 wherein the indication of the mounting location includes a recess on the first major face.

4. The packaging of claim 1 wherein the one or more tabs include at least two tabs, the at least two tabs are configured to bend about the portion of at least one of the one or more first urological devices.

5. The packaging of claim 4 wherein the at least two tabs are configured to connect together.

6. The packaging of claim 5 wherein a first of the at least two tabs includes a first slit on a distal portion thereof configured to form an opening in the distal portion of the first tab, and a second of the at least two tabs includes a second slit on a distal portion thereof configured to form a flap extending from the distal portion of the second tab, the flap being configured to be inserted into the opening.

7. The packaging of claim 1 wherein the portion of the first tubular member, which includes the open end, extends out of a space defined by an inside diameter that is formed by an innermost loop of the first tubular member.

8. The packaging of claim 7 wherein the portion of the first tubular member, which terminates at the open end, lies on another portion of the first tubular member.

9. The packaging of claim 1 wherein two or more portions of at least one of the one or more tubular members are connected together.

10. The packaging of claim 1, further comprising one or more additional tubular members secured to the second major face of the base, at least one of the one or more additional tubular members having a looped or coiled configuration, the one or more additional tubular members defining corresponding one or more internal spaces each sized and configured to secure one or more second urological devices.

11. The packaging of claim 1 wherein the one or more tabs are sized and configured to secure at least a portion of at least one of the one or more first urological devices or one or more second urological devices near one or more of the first major face or the second major face.

12. The packaging of claim 1 wherein the one or more tabs are configured to bend such as to extend outward from one or more of the first major face or the second major face.

13. A urological kit, comprising: a urological kit packaging including:
    a base including sheet material having generally opposing first and second major faces defining a thickness of the base by a distance therebetween; one or more tubular members including a first tubular member, the one or more tubular members secured to the first major face of the base, at least the first tubular member of the one or more tubular members having a coiled configuration with loops thereof located generally in a single plane, a portion of the first tubular member terminating at an open end and extending out of the single plane and over another portion of the first tubular member, each of the one or more tubular members defining an internal space; and two or more tabs secured to or integrated with the base;

a second tubular member having a looped or coiled configuration having loops thereof located in the single plane, a portion of the second tubular member terminating at an open end and extending out of the single plane and over another portion of the second tubular member;

and a plurality of urological devices including a stone removal basket having a handle and a wire, at least some of the plurality of urological devices including an elongated portion secured within a corresponding internal space of the one or more internal spaces of the one or more tubular members, the handle of the stone removal basket is secured near the first major face by at least two of the two or more tabs.

14. The urological kit of claim 13 wherein the wire of the stone removal basket is secured within an internal space of the one or more internal spaces of the one or more tubular members.

15. The urological kit of claim 14 wherein the two or more tabs wrap around a portion of the handle.

16. The urological kit of claim 15 wherein one of the two or more tabs includes an opening and another of the two tabs includes a flap positioned inside the opening and securing together the two or more tabs.

17. The urological kit of claim 13 wherein the plurality of urological devices includes a guidewire secured within an internal space of the one or more internal spaces of the one or more tubular members.

18. The urological kit of claim 13 wherein the plurality of urological devices includes a ureteral stent secured in a plastic bag or container, the plastic bag or container being secured between the first major face and at least two more of the tabs of the one or more tabs.

19. The urological kit of claim 13, further comprising one or more additional tubular members secured to the second major face of the base, at least some of the elongated portions of the plurality of urological devices being secured within corresponding internal spaces of the one or more additional tubular members.

20. A system for urological procedures, the system comprising:
a foldable base including a first side and a second side foldably connected together by a fold line with each other; one or more tubular members including a first tubular member secured to one or more of the first side of the foldable base, and a second tubular member second tubular member secured to the second side, at least one of the first or second tubular members having a looped or coiled configuration, each of the first or second defining an internal space; and one or more tabs secured to or integrated with one or more of the first side or the second side of the foldable base, the one or more tabs being sized and configured to secure at least a portion of a urological device.

21. The system of claim 20, further comprising one or more urological devices secured to the foldable base on one or more of the first side or the second side thereof.

22. The system of claim 21 wherein at least one of the one or more urological devices includes an elongated portion secured within the internal space of at least one of the first or second tubular members.

23. The system of claim 21 wherein at least a portion of at least one of the one or more urological devices is secured to the foldable base by at least one of the one or more tabs.

24. The packaging of claim 1 wherein the portion of the second tubular member, which terminates at the open end, lies on the another portion of the second tubular member.

25. The packaging of claim 24 wherein the portion of the second tubular member, which terminates at the open end, extends over a portion of at least another tubular member of the one or more tubular members.

26. The packaging of claim 1 wherein the one or more tubular members include at least two tubular members bonded together.

* * * * *